United States Patent [19]
Atkins et al.

[11] Patent Number: 4,866,020
[45] Date of Patent: Sep. 12, 1989

[54] LITHIATED CLAYS AND USES THEREOF

[75] Inventors: Martin P. Atkins, Middlesex; James A. Ballantine; John H. Purnell, both of Swansea; John Williams, Gwynedd, all of United Kingdom

[73] Assignee: The British Petroleum Company p.l.c., London, England

[21] Appl. No.: 170,725

[22] Filed: Mar. 21, 1988

[30] Foreign Application Priority Data

Mar. 26, 1987 [GB] United Kingdom ................. 8707309

[51] Int. Cl.$^4$ ............................................. B01J 21/16
[52] U.S. Cl. ........................................ 502/84; 502/80
[58] Field of Search ..................................... 502/80, 84

[56] References Cited

U.S. PATENT DOCUMENTS 4,367,163  1/1983  Pinnavia et al. ................. 252/455 R
4,436,832  3/1984  Jacobs et al. .......................... 502/84

FOREIGN PATENT DOCUMENTS 0040276  11/1981  European Pat. Off. .
2111193   9/1972  Fed. Rep. of Germany .
2151603   7/1985  United Kingdom ........... 423/328 M
2154998   9/1985  United Kingdom .................. 502/80

Primary Examiner—Carl F. Dees
Attorney, Agent, or Firm—Brooks Haidt Haffner & Delahunty

[57] ABSTRACT

A novel family of layered clays, called lithiated clays is disclosed. The novel layered clays are characterized by the replaceable hydrogens of the hydroxyl groups within the structure of a layered clay being replaced by lithium. A method of manufacturing the lithiated clays is disclosed together with their use as catalysts.

5 Claims, No Drawings

LITHIATED CLAYS AND USES THEREOF

The present invention relates generally to layered clays and in particular to modified layered clays, their preparation and their use as catalysts in reactions capable of catalysis by protons.

Broadly, the clay minerals are all aluminosilicates. Two groups, the amorphous (I) and the crystalline (II) may generally be distinguished. The present invention is not concerned with the amorphous clays, otherwise known as the allophanes, largely because they are of comparatively little interest as catalysts. Clay minerals of group (II) can be broadly subdivided into the following four groups:

(a) Two-layer sheet types, such as the kandites. In these, the sheets are composed of units of one layer of silica tetrahedrons and one of alumina octahedrons, each double layer sheet being then separated from the next by an interlamellar space of 8 Angstroms or more.

(b) Three-layer sheet types, such as the smectites, micas and vermiculites. Here the sheet structures are composed of successive layers of tetrahedral silica, octahedral alumina and tetrahedral silica (TOT). The central layer of each sheet (O-layer) may be dioctahedral or trioctahedral and again the sheets are separated by an interlamellar space.

This group is further sub-divided into:
   (i) expanding (swelling), eg montmorillonite, vermiculite, and some brittle micas, and
   (ii) non-expanding, eg pyrophyllite, illite and micas.

(c) Regular mixed layer types, such as the chlorites.

(d) Chain structure types with chains of silica tetrahedrons linked by octahedral groups of oxygens and hydroxyls with Al or Mg atoms, for example sepiolite.

Of these, clays of type (d) are of no interest in the context of the present invention, which is principally though not exclusively concerned with clays of type (b). The idealised basic structure of clays of type (b) is that of pyrophyllite which has the basic formula $Si_8Al_4O_{20}(OH)_4$ but the important members of the group are the montmorillonites, vermiculites and micas. The TOT structure is obviously fully charge balanced in pyrophyllite and thus, since there is no charge excess or deficiency, the interlamellar space is neutral and is, in nature, occupied by water molecules. In practice many variants of this structure occur for a variety of reasons. For example the central octahedral layer may be occupied not by four 3-valent cations (eg $Al^{3+}$) but by six 2-valent cations (eg $Mg^{2+}$). The former comprise the class of dioctahedral clays, the latter trioctahedral clays, which it is readily apparent, also have no charge deficiency or excess in the sheet by analogy with pyrophyllite. Furthermore, only partial replacement, ie one $M^{2+}$ for one $M^{3+}$, results in a residual surplus of negative charge in the structure and this leads to the necessity to introduce balancing cations into the interlamellar space together with solvent. Moreover, substitution of $Al^{3+}$ for $Si^{4+}$ in the tetrahedral layer also leading to residual negative charge is possible. This leads to the formation of alternative groups or sub-groups depending upon the identities and extents of ion substitution. Thus, a general representation of the available variants on the pyrophyllite structure is:

$$M^{z+}{}_{(x+y)/z}(Y)_n[(M_I{}^{2+}, M_{II}{}^{3+})_{(6-y)}{}^{+}(OH)_2Si_{4-x}Al_xO_{10}]^{(x+y)-}$$

here $M^{z+}{}_{(x+y)/z}$ represents interlamellar (balancing) cations, Y represents $H_2O$ (or other swelling liquid) and the square bracket describes the silicate layer. x and y are the charges of the cations substituted in the tetrahedral layer and octahedral layers, respectively. It is the flexibility of this formulation that allows such a range of values of x and y, and hence of (x+y) and so defines the various mineral types and their properties. The following annotated table for a series of related materials, all having $Al^{3+}$ as the dominant ion in the octahedral layer, illustrates the point. All, of corse, are by definition dioctahedral varieties.

| x + y     | Group       | Sub-Group       | Variety         |
|-----------|-------------|-----------------|-----------------|
| 0         | —           | —               | Pyrophyllite    |
| 0.25–0.55 | Smectites   | Montmorillonite | Montmorillonite |
| 0.55–0.69 | Vermiculites| Vermiculite     | Vermiculite     |
| 0.66–0.88 | Mica        | Illite          | Illite          |
| 1.8–2.0   | Mica        | Mica            | Muscovite       |

Although pyrophyllite (x+y=0) is non-swelling, all others of (x+y) up to about 0.7 will undergo swelling, those of x+y greater than about 0.7 are non-swelling.

The exchangeable cations in the interlamellar space, which balance the residual negative layer charge, are normally hydrated but, in fact, a host of solvating molecules may be intercalated along with, or in place of, water. The number of exchangeable cations, as reflected by the Cation Exchange Capacity (C.E.C.), is primarily fixed by the layer charge, with defects at layer edges perhaps adding a further 5–10%.

It is now very well documented that certain cation-exchanged, for example $Al^{3+}$ or $H^{3+}$-exchanged, layered clays are very strong Bronsted acids which property renders them as catalysts in a wide variety of reactions capable of catalysis by protons, see for example our European patent publication Nos. 0031687 and 0031252. Two problems associated with the use of layered clays as catalysts in certain reactions is their instability, caused by the tendency of the layers to collapse at high temperatures and under hydrothermal conditions, with associated loss of catalytic activity and secondly their granule instability in the presence of polar solvents, e.g. water and methanol. Attempts to improve the stability of layered clays have involved the introduction into the interlamellar space of various metal compounds, thereby forming "pillars". Representative of the art relating to pillared layered clays may be mentioned U.S. Pat. Nos. 4,216,188; 4,248,739; 4,510,257 and 4,515,901 for example. Although such methods demonstrably provide layered clays of improved stability, this is offset to some extent by a loss in catalytic activity as compared with the activity of non-pillared layered clays. Morever, pillared clays are non-swelling.

Our copending UK application publication No. 2179563 (BP Case No. 6116) discloses a layered clay in which the interlamellar charge, as defined by its C.E.C., is sufficient only to permit expansion of the sheets to accommodate a sinle liquid layer and its production by (i) cation-exchanging a layered clay with a solution comprising a source of either alkali metal or alkaline earth metal cations and a source of ions capable of migrating into vacant cation-exchangeable sites in the octahedral layer of the clay, exchanging alkali or alkaline earth metal cations with catalytically active cations and finally heating the cation-exchanged clay at elevated temperature, the cation-exchange and heating being effected under conditions which do not destroy the lamellar structure of the clay, or (ii) by effecting a single cation-exchange with catalytically active cations and a source of ions capable of migrating into vacant cation-exchangeable sites. An ion capable of migrating into vacant cation-exchangeable sites in the octahedral layer of the clay is lithium.

A disadvantage of these materials is that they have low cation exchange capacity which limits their use as catalysts and other applications.

A new class of modified clays has now been developed with full cation exchange capacity. These materials therefore have the desirable exchange attributes of conventional layered clays whilst possessing the particle stability exhibited by the materials defined in UK Application 2179563.

Accordingly in one embodiment the present invention provides a lithiated layered clay in which the replaceable hydrogens of the hydroxyl groups within the structure of a layered clay are replaced by lithium.

In another embodiment the present invention provides cation-exchanged forms ofthe aforesaid lithiated layered clays.

In a further embodiment the present invention also provides a process for the production of a lithiated layered clay as aforesaid which process comprises the steps of:

(A) Cation-exchanging a layered clay with a source of lithium cations to produce a lithium-exchanged layered clay, and (B) therefore reacting the lithium-exchanged layered clay with either an organic base or ammonia at a temperature and for a time such that replaceable hydrogen atoms of hydroxyl groups within the structure of the lithium-exchanged layered clay are replaced by lithium atoms to form —O—Li linkages within the structure.

During stage (B), the replaceable hydrogen atoms of the hydroxyl groups in the structure are converted according to the reaction $Li^+ + -OH \rightarrow H^+ + -OLi$ and the protons are extracted into the interlamellar space by the action of heat and base.

It is thereafter preferred to cation-exchange the lithiated clay obtained in step (B).

In a preferred embodiment of the process for producing the lithiated layered clay steps (A) and (B) may be combined into a single step in which the layered clay, the source of lithium cations and the base are reacted together under the aforesaid conditions.

As regards the layered clay starting material, both natural and synthetic layered clays may be employed. The layered clay may be any of the layered clays (a) to (c) as hereinbefore described, though dioctahedral clays may be used in preference to trioctahedral clays. Preferably the layered clay is a smectite or vermiculite, even more preferably a smectite, for example a montmorillonite. A suitable form of montmorillonite is bentonite. The exchangeable cation of the layered clay may be for example sodium or hydrogen, though it could be any of a variety of other cations.

The cation-exchange (Step A of the two-step process) may be accomplished by any of the techniques conventionally employed for this purpose. Suitably cation-exchange may be accomplished by contacting the layered clay with a solution of lithium cations under cation-exchange conditions. Preferably the solution is an aqueous solution. The source of lithium cations may suitably be a lithium salt, for example lithium chloride or lithium nitrate. The cation-exchange must be accomplished at a temperature which does not collapse the layered structure of the clay, suitably at a temperature below 50° C., preferably below 30° C., for example ambient temperature. Techniques for separating the lithium-exchanged clay from the ion-exchange media and excess ions are well-known. Any solid/liquid separation procedure may be used to recover the lithium-exchanged layered clay.

In step (B) the lithium-exchanged layered clay produced in step (A) is reacted with either an organic base or ammonia. Suitable organic bases include pyridine, benzylamine, piperidine and cyclohexylamine, preferably benzylamine and cyclohexylamine. If ammonia is used it may be in the form of liquid anhydrous ammonia, an ammonia solution or gaseous ammonia. When used in solution form it is preferred to use an aqueous solution, though alcoholic solutions for example may be employed if desired. The use of gaseous ammonia is preferred because it facilitates the production of the products on a commercial scale.

The temperature at which replaceable hydrogen atoms of hydroxyl groups within the structure of the clay are replaced by lithium atoms will depend upon a number of factors including the nature of the starting layered clay but will generaly not be less than 200° C. Typically the time required to produce the lithiated clay at 200° C. is about 8 hours, though longer or shorter times may be employed. Employing higher temperatures, for example a temperature in the range from 200° to 500° C., the time required to produce the lithiated clay may be correspondingly shortened. Alternatively, the amount of lithium introduced into the clay may be increased.

It may be desirable to wash the clay produced in step (A), suitably with distilled water, before proceeding to step (B).

As mentioned hereinbefore steps (A) and (B) may be advantageously combined into a single step by reacting the layered clay, an excess of lithium cations and the base, preferably ammonia, under the aforesaid conditions. Typically a five fold excess of lithium cations is used based upon the exchange capacity of the clay.

For use as a catalyst it is preferred to convert the lithiated layered clay so-obtained to cationic forms having greater catalytic activity. This may suitably be achieved by cation-exchange in a conventional manner or by calcining the $NH_4^+$ form of the clay produced as hereinbefore described. Examples of catalytically active cations include hydrogen ions and metal ions, for example aluminium, chromium, cobalt, nickel, iron, copper and vanadium cations. The hydrogen ion-exchanged lithiated clay may be produced, for example, either by heating the ammonium-exchanged form or by cation-exchange with an aqueous solution of a protonic acid.

The lithiated clay so-produced is stable to polar solvents, for example methanol, under conditions which cause breakdown of the layered clay starting material. In this respect it is similar to pillared clays. However, unlike pillared clays, it retains its ability to swell and its catalytic activity in cation-exchanged forms is comparable with that of the correspondingly cation-exchanged layered clay.

In view of their stability in water and organic solvents and their high catalytic activity the cation-exchanged forms of the lithiated layered clays are particularly suitable as catalysts in processes wherein a conventional layered clay has a tendency to breakdown, for example in the production of ethers such as methyl tertiary butyl ether (MTBE) and glycol ethers. They also find utility in the whole range of proton-catalysed reactions.

Thus the lithiated layered clays may be used as catalysts in a wide variety of reactions capable of catalysis by protons, including the following:

(i) a process for the production of an ester by reacting either an olefin or an olefin oxide with a carboxylic acid, (ii) a process for the production of an ether by reacting either an olefin or an olefin oxide with an alcohol, (iii) a process for the production of an alcohol by reacting an olefin with water, (iv) a process for the production of an alkyl aromatic hydrocarbon by reacting an aromatic hydrocarbon with an alkylating agent selected from olefins and $C_2$ or higher alcohols, (v) a process for the transalkylation of alkyl aromatic hydrocarbons, (vi) a process for the dealkylation of alkyl aromatic hydrocarbons, (vii) a process for the conversion of either a primary or secondary aliphatic alcohol into an ether, and (viii) a process for the conversion of an olefin oxide into an ether.

The aforesaid are only representative of the variety of reactions capable of catalysis by protons to which the process of the present invention is applicable. Conditions under which such processes are operated are by now well established in the art, representative of which may be mentioned the aforesaid EP-A-0031687 and EP-A-0031252.

The process of the present invention will now be further illustrated by reference to the following Examples.

PREPARATION OF CATION-EXCHANGED LITHIATED LAYERED CLAYS (I) Using Organic Bases

Lithiated Layered Clay (A)—(Example 1)

A lithium-exchanged montmorillonite (C.E.C.—84 meq/100 g) was prepared by stirring sodium montmorillonite in aqueous lithium chloride (room temperature, ca 2 hours) followed by decantation and water washing. Samples were heated in a batch reactor with cyclohexylamine for 6 hours at respectively 220° C. and 267° C. The lithiated layered clays were recovered and a portion of each examined by thermal gravimetric analysis (TGA).

It was found that the organic base was protonated with the protons coming from structural hydroxyl groups. The TGA studies confirmed that the concentration of protonated base was approximately equivalent to the amount of lithium retained in the clay structure as shown in Table 1.

TABLE 1

| Determination | T = 220° C. | T = 267° C. |
|---|---|---|
| Protonated cyclohexylamine (meq/100 g) | 53.2 | 60 |
| Structural Li (meq/100 g) | 54.2 | 61.6 |

(II) Using Inorganic Bases

Lithiated Layered Clay (B)—Example 2

A 100 g batch of the lithium-exchanged montmorillonite (C.E.C.=82 meq/100 g) was heated in an autoclave with aqueous ammonia (36% w/v) for 8 hours at 200° C. The lithiated montmorillonite was recovered and washed with distilled water to remove excess $NH_3$ and then exchanged with $NH_4^+$ ions to produce the $NH_4^+$-exchanged lithiated montmorillonite.

TGA, CEC and atomic absorption analyses were made on samples of the product and a portion was exchanged with $Zr^{4+}$ to produce a $Zr^{4+}$ lithiated layered montmorillonite. XRD, CEC, Solvent Stability and TGA determinations were carried out on the product.

Lithiated Layered Clays (C)-(E)—Examples 3 to 5

Using appropriate reagents, and the remainder of the $NH_4^+$-exchanged precursor of the clay (B), $Fe^{3+}$ lithiated layered montmorillonite (C), $Al^{3+}$ lithiated layered montmorillonite (D) and $H^+$ lithiated layered montmorillonite (E) were produced and the same determinations made.

The results of these determinations are given in Table 2.

TABLE 2

| | | PROPERTY | | | | | | |
|---|---|---|---|---|---|---|---|---|
| | | XRD | | FES | TGA | | | |
| Sample | Cation | $d_{001}$ | Glycerol treated $d_{001}$ | Lattice Li (mmol/100 g) | Phys $H_2O$ (% wt) | Chem $H_2O$ (% wt) | CEC (meq/100 g) | Stability in MeOH |
| B (Ex 2) | $Zr^{4+}$ | 16.52 | ND | 35.3 | 11.2 | 2.6 | 38.3 | Stable |
| C (Ex 3) | $Fe^{3+}$ | 13.19 | ND | 35.3 | 9.1 | 2.2 | 66.5 | Stable |
| D (Ex 4) | $Al^{3+}$ | 15.50 | ND | 35.3 | 10.7 | 2.8 | 77.3 | Stable |
| E (Ex 5) | $H+$ | 13.92 | ND | 35.3 | 9.5 | 2.2 | 64.3 | Stable |
| Montmorillonite (CT 1) | $Al^{3+}$ | 15.27 | ND | zero | 14.5 | 2.2 | 71.9 | Unstable |
| $Al_{13}$ pillared lithiated montmorillonite (CT 2) | | 15.71 | 17.39 | 35.3 | ND | ND | 39.5 | |

ND = Not Determined

Lithiated Layered Clays (F)-(J)—Examples 6 to 10

Aluminium-exchanged lithiated layered clays were prepared from montmorillonite KSF(F) (Example 6), montmorillonite 'Cheto' (G) (Example 7), gelwhite 'L' (H) (Example 8), beidellite (I) (Example 9) and barasym (J) (Example 10) using the lithiation process of Example 2 followed by (a) ammonium exchange and (b) thereafter aluminium exchange and the same determinations made.

The results of these determinations for both the unlithiated starting materials and the lithiated products are given in Table 3.

Pelletised forms of the aluminium-exchanged lithiated layered clays were found to be indefinitely stable in methanol at room temperature. All examples showed substantial lithiation.

TABLE 3

| | Al$^{3+}$-exchanged layered clay | | | | | | | | | |
|---|---|---|---|---|---|---|---|---|---|---|
| | KSF | | CHETO | | GELWHITE | | BEIDELLITE | | BARASYM | |
| PROPERTY | Un-lithiated | Lithiated (Ex 6) | Un-lithiated | Lithiated (Ex 7) | Un-lithiated | Lithiated (Ex 8) | Un-lithiated | Lithiated (Ex 9) | Un-lithiated | Lithiated (Ex 10) |
| C.E.C. (meq/100 g) | 59.9 | 67.3 | 111.4 | 107.9 | 77.8 | 84.2 | 39.9 | 44.6 | 50.0 | 53.0 |
| Lattice Li (meq/100 g) | — | 19.9 | — | 54.4 | — | 56.0 | — | 33.9 | — | 43.0 |
| % Chemical H$_2$O (wt %) | less than 1.3 | 0.9 | 2.5 | 2.6 | 2.6 | 2.7 | 3.1 | 2.7 | greater than 1.2 | greater than 1.0 |

Lithiated Layered Clays (K)–(M)—Examples 11–13

The procedure of Example 2 was repeated except that gaseous ammonia was used instead of aqueous ammonia, a series of temperatures, i.e. 200° C. (K) (Example 11), 250° C. (L) (Example 12) and 300° C. (M) (Example 13) was employed and the cation-exchange was with Al$^{3+}$ ions. The same determinations were made on the resulting clays.

The results of the determination are given in Table 4.

TABLE 4

| Example | Clay Sample | Preparation Temperature (°C.) | C.E.C. (meq/100 g) | Lattice Li (mmol/100 g) | Chemical Water |
|---|---|---|---|---|---|
| 11 | Al$^{3+}$-lithiated montmorillonite | 200 | 70.3 | 18.8 | 2.3 |
| 12 | Al$^{3+}$-lithiated montmorillonite | 250 | 70.2 | 32.1 | 2.3 |
| 13 | Al$^{3+}$-lithiated montmorillonite | 300 | 68.4 | 40.4 | 2.5 |

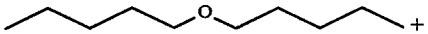

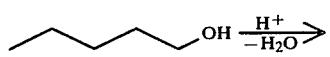

A portion of the cation-exchanged lithiated layered clay was placed in a stainless steel reactor of internal volume 20 ml and 3 ml of n-pentanol was added. The sealed reactor was placed in an oven thermostatically controlled at 200° C. After 14 hours the reactor was cooled and its contents analysed by gas chromatography.

The results are given in Table 5.

TABLE 5

| | | PRODUCT YIELDS | | | | |
|---|---|---|---|---|---|---|
| Example | Cation | PENTENE (wt %) | 1,2-ETHER (wt %) | 1,1-ETHER (wt %) | 1,1-ETHER/ PENTENE | 1,2-ETHER/ PENTENE |
| 14 | H$^+$ (A) | 5.0 | 2.6 | 45.3 | 9.1 | — |
| 15 | H$^+$ (B) | 0.03 | 0.2 | 0.74 | 24.7 | — |
| 16 | H$^+$ (C) | 3.2 | 2.3 | 29.4 | 9.2 | — |
| 17 | H$^+$ (D) | 0.08 | 0.2 | 1.13 | 14.1 | — |
| 18 | Zr$^{4+}$ (E) | 5.2 | 3.0 | 36.8 | 7.1 | 0.6 |
| 19 | Fe$^{3+}$ (F) | 1.9 | 1.6 | 13.3 | 7.2 | 0.8 |
| 20 | Al$^{3+}$ (G) | 7.4 | 3.7 | 42.8 | 5.8 | 0.5 |
| 21 | H$^+$ (H) | 9.9 | 4.1 | 46.0 | 4.7 | 0.4 |
| CT 3 | Al$^{3+}$ montmorillonite H$^+$-exchanged | 7.7 | 3.8 | 41.7 | 5.4 | 0.5 |
| CT 4 | Al$_{13}$ pillared lithiated montmorillonite | 1.2 | 0.8 | 12.1 | 10.1 | 0.7 |

CATALYST TESTING

Examples 14 to 21 and Comparison Test 3 and 4

The reaction may be represented by the following equation:

$$\sim\!\!\sim\!\!\sim\!\!\sim\!\!\text{OH} \xrightarrow[-H_2O]{H^+}$$

Examples 22–26 and Comparison Tests 5 to 9

The procedure of Examples 14–21 were repeated using the Al$^{3+}$-exchanged lithiated layered clay products of Examples 6 to 10 For comparison unlithiated layered clays (exchanged with aluminium) were of also tested.

The results are given in Table 6.

TABLE 6

| PRODUCT YIELDS (wt %) | $Al^{3+}$-exchanged layered clay | | | | | | | | | |
|---|---|---|---|---|---|---|---|---|---|---|
| | KSF | | CHETO | | GELWHITE | | BEIDELLITE | | BARASYM | |
| | Un-lithiated (CT 5) | Lithiated (Ex 22) | Un-lithiated (CT 6) | Lithiated (Ex 23) | Un-lithiated (CT 7) | Lithiated (Ex 24) | Un-lithiated (CT 8) | Lithiated (Ex 25) | Un-lithiated (CT 9) | Lithiated (Ex 26) |
| 1,1-Ether | 37.7 | 20.6 | 40.7 | 36.0 | 38.2 | 33.0 | 23.2 | 5.2 | 19.1 | 10.7 |
| 1,1-Ether/Pentene | 6.3 | 7.6 | 4.1 | 4.7 | 4.0 | 4.5 | 5.4 | 5.8 | 11.9 | 10.7 |

Examples 27–29

The procedure of Examples 14–21 was repeated using the $Al^{3+}$-exchanged lithiated montmorillonite products of Examples 11 to 13.

The results are given in Table 7.

TABLE 7

| | PRODUCTS | |
|---|---|---|
| Example | Yield of 1,1-Ether (wt %) | 1,1-Ether/Pentene |
| 27 | 46.8 | 4.9 |
| 28 | 47.5 | 5.4 |
| 29 | 45.5 | 5.7 |

Examples 30 to 33 and Comparison Test 10

Benzene was alkylated with isopropanol as at 200° C. for 4 hours under batch conditions using the clay products of Examples 2 to 5, i.e. products (B) to (E), as catalysts using identical proportions of reactants.

The analyses for cumene and ethyl benzene are given in Table 8.

TABLE 8

| | | PRODUCTS | |
|---|---|---|---|
| Example | Catalyst | Cumene (wt %) | Ethyl benzene (ppm) |
| 30 | (B) - $Zr^{4+}$ | 8.5 | 2 |
| 31 | (C) - $Fe^{3+}$ | less than 5.0 | 1 |
| 32 | (D) - $Al^{3+}$ | 13.5 | 59 |
| 33 | (E) - $H^+$ | 13.5 | 3 |
| CT 10 | $H^+$—$Al_{13}$pillared montmorillonite | less than 1.0 | Not determined |

Examples 34 to 37 and Comparison Test 11

2-methylbutene-1 was reacted with methanol at 120° C. for 1 hour under batch conditions using the lithiated clay products of Examples 2 to 5, i.e. products (B) to (E) as catalysts using identical proportions of reactants.

The analysis of the products is given in Table 9.

TABLE 9

| | | PRODUCTS | | |
|---|---|---|---|---|
| Example | Catalyst | t-amyl-methylether (wt %) | 2-methyl butene-2 (wt %) | Unreacted 2-methyl butene-1 (wt %) |
| 34 | (B) - $Zr^{4+}$ | 15.6 | 11.9 | 48.6 |
| 35 | (C) - $Fe^{3+}$ | 18.1 | 15.2 | 41.8 |
| 36 | (D) - $Al^{3+}$ | 16.5 | 12.0 | 47.8 |
| 37 | (E) - $H^+$ | 18.3 | 16.2 | 42.6 |
| CT 11 | $H^+$—$Al_{13}$ pillared lithiated montmorillonite | 9.6 | 6.5 | 57.0 |

Example 38 to 42 and Comparison Tests 12 to 16

The procedure of Examples 34 to 37 was repeated using the $Al^{3+}$-exchanged lithiated clay products of Examples 6 to 10 and using the corresponding unlithiated layered clays (Comparison Tests 12 to 16).

The analyses for t-amylmethylether (TAME) are given in Table 10.

TABLE 10

| | $Al^{3+}$-exchanged layered clay | | | | | | | | | |
|---|---|---|---|---|---|---|---|---|---|---|
| | KSF | | CHETO | | GELWHITE | | BEIDELLITE | | BARASYM | |
| | Un-lithiated (CT 12) | Lithiated (Ex 38) | Un-lithiated (CT 13) | Lithiated (Ex 39) | Un-lithiated (CT 14) | Lithiated (Ex 40) | Un-lithiated (CT 15) | Lithiated (Ex 41) | Un-lithiated (CT 16) | Lithiated (Ex 42) |
| TAME yield (wt %) | 19.9 | 15.4 | 14.0 | 12.6 | 15.4 | 16.4 | 18.7 | 12.5 | 15.1 | 17.0 |

Examples 43 to 45

The procedure of Examples 34 to 37 was repeated using the $Al^{3+}$-exchanged lithiated clay products of Examples 11 to 13.

The analyses for t-amylmethylether are given in Table 11.

TABLE 11

| Example | TAME (wt %) |
|---|---|
| 43 | 17.5 |
| 44 | 17.8 |
| 45 | 19.3 |

Example 46

The $Al^{3+}$-exchanged lithiated montmorillonite KSF of Example 6 was refluxed with methanol for 1.5 hours. No breakdown of the clay particles was observed.

Example 47

Samples of the $Al^{3+}$-exchanged lithiated montmorillonite (D) of Example 4 and the $Li^+$-exchanged montmorillonite starting material were analysed by IR spectroscopy.

The IR spectra confirm that free structural hydroxyl groups are reduced by up to ⅔ intensity.

Example 48

Samples of each of the $Al^{3+}$-exchanged lithiated montmorillonite (D) of Example 4 and the $Li^+$-exchanged montmorillonite starting material were analysed by $^7Li$ NMR.

The lithiated clay showed a featureless $^7Li$ NMR line indicating that Li was in the sheet structure in which the assymetrical environment causes line broadening.

The $Li^+$-exchanged clay had two different $^7Li$ resonances overlapped. A broad NMR resonance underneath was similar to those of the lithiated clay, implying that very small amounts of $Li^+$ had entered into the sheet structure. A narrow resonance came from a symmetrical $^7Li$ environment, i.e. exchanged $Li^+$ ion in interlayers.

We claim:

1. A lithiated layered clay in which the replaceable hydrogens of the hydroxyl groups within the structure of a layered clay are replaced by lithium.

2. A lithiated layered clay produced by
   (a) cation-exchanging a layered clay with a source of lithium cations to produce a lithium exchanged layered clay and
   (b) thereafter reacting the lithium exchanged layered clay with either an organic base or ammonia at a temperature and for a time such that replaceable hydrogen atoms of hydroxyl groups within the structure of the lithium exchanged layered clay are replaced by lithium atoms to form —OLi linkages within the structure.

3. A lithiated layered clay as claimed in claim 2 wherein steps
   (a) and (b) are performed in a single reaction zone by heating a mixture of the layered clay, the organic base or ammonia, and excess lithium cations.

4. A lithiated layered clay as claimed in claim 1 wherein the layered clay is a smectite.

5. Cation-exchanged forms of a lithiated clay as defined in any one of claims 1 to 4.

* * * * *